United States Patent [19]

Bastiaansen et al.

[11] Patent Number: 5,428,079
[45] Date of Patent: Jun. 27, 1995

[54] SOLUTION OF ULTRA-HIGH MOLECULAR WEIGHT POLYETHYLENE

[75] Inventors: Cornelis W. M. Bastiaansen, Maastricht; Joseph A. P. M. Simmelink, Eijsden, both of Netherlands

[73] Assignee: DSM N.V., Netherlands

[21] Appl. No.: 842,139

[22] PCT Filed: Jul. 30, 1991

[86] PCT No.: PCT/NL91/00140

§ 371 Date: Jun. 28, 1992

§ 102(e) Date: Jun. 28, 1992

[87] PCT Pub. No.: WO92/02668

PCT Pub. Date: Feb. 20, 1992

[30] Foreign Application Priority Data

Aug. 1, 1990 [NL] Netherlands ................. 9001745

[51] Int. Cl.⁶ .................................................. C08J 3/28
[52] U.S. Cl. ..................................... 522/161; 524/528; 524/468; 524/470; 524/490; 525/240; 526/352
[58] Field of Search ....................... 522/161; 526/352; 524/528, 468, 470, 490; 525/240

[56] References Cited

U.S. PATENT DOCUMENTS

| | | | |
|---|---|---|---|
| 2,908,659 | 10/1959 | Shashoua | 260/32.6 |
| 3,956,253 | 5/1976 | Braun | 526/352 |
| 4,598,128 | 7/1986 | Randall et al. | 525/240 |
| 4,962,167 | 10/1990 | Shiraishi et al. | 526/125 |
| 5,066,755 | 11/1991 | Lemstra | 526/348 |

FOREIGN PATENT DOCUMENTS

| | | |
|---|---|---|
| 0167187 | 1/1986 | European Pat. Off. . |
| 0215507 | 3/1987 | European Pat. Off. . |
| 0229477 | 7/1987 | European Pat. Off. . |

OTHER PUBLICATIONS

Fred W. Billmeyer, Jr. Textbook of Polymer Science, 1984, p. 151 3rd edition.

*Primary Examiner*—David W. Wu
*Attorney, Agent, or Firm*—Cushman Darby & Cushman

[57] ABSTRACT

Solution of UHMWPE in an organic solvent having a total PE concentration of at least 15% by weight and in which some of the PE present is crosslinked.

19 Claims, 1 Drawing Sheet

SOLUTION OF ULTRA-HIGH MOLECULAR WEIGHT POLYETHYLENE

The invention relates to a solution of ultra-high molecular weight polyethylene in an organic solvent.

From "Ullmanns Encyclopedia of Industrial Chemistry", Vol. A10, (1987), page 522, paragraph 2.1.4 it is known to process polymers which cannot be processed as a melt, for example by spinning or extruding, in the form of a solution of the polymer in a suitable solvent. In particular, this applies in the case of polymers having a high molecular weight. In the said reference it is also pointed out that the concentration of the polymer in the solution must not be too low, since this lowers the production and increases the costs of solvent recovery. It is known that the viscosity of solutions of ultra-high molecular weight polymers increases with the concentration for a constant molecular weight of the polymer and with the molecular weight for a constant concentration. A disadvantage of these solutions is that they already have such a high viscosity at a low concentration that the solutions frequently cannot be processed, or can be processed only with difficulty, using the conventional equipment. In particular in the case of the processing of ultra-high molecular weight polyethylene, a very well known and widely used example of an ultra-high molecular weight polymer which hereinafter is indicated by UHMWPE, the concentration which is still permissible with regard to this restriction is frequently in conflict with economic operation because of the large amount of solvent to be removed and further processed, and the relatively low yield of processed UHMWPE.

The aim of the invention is to provide a solution of UHMWPE which does not have this disadvantage or has this disadvantage to a considerably lesser extent.

This aim is achieved according to the invention in that the polyethylene concentration is at least 15% by weight and the solution contains a crosslinked ultra-high molecular weight polyethylene.

When mention is made in this description of a solution, this is also understood to be, in addition to a composition consisting of non-crosslinked polyethylene, which is molecularly distributed in a solvent for polyethylene, a homogeneous composition of this type in which only crosslinked polyethylene is present or in which crosslinked polyethylene and uncrosslinked polyethylene occur alongside one another.

The solution according to the invention is found to possess an appreciably more favourable relationship between the total polyethylene concentration and the viscosity than the known solution. Consequently, more concentrated solutions than were possible hitherto can be processed using conventional equipment or, stating the advantage of the solution according to the invention in another way, the processing of solutions having a specific UHMWPE concentration places lesser demands on the processing equipment. In practice, what is achieved by this means is that, as a result of the higher permissible concentration, for a given flow rate in the processing equipment, for example an extruder, per unit time a greater amount of the polymer is converted into the desired product and a smaller amount of solvent has to be processed. This makes a considerably more economic process possible.

A further advantage of the solution according to the invention is that, for a chosen concentration, the service life of the equipment used for processing can be appreciably prolonged as a result of the now lower operating pressure, which is built up during spinning or extruding of the solution.

It is known from U.S. Pat. No. 2,908,659 to add specially prepared crosslinked particles called "d-microgels" to a solution of a polymer in order to introduce certain properties into products produced with the aid of said solution. Of such properties only dyeability is explicitly mentioned. The low-concentration solutions of UHMWPE or other high molecular weight polymers are not mentioned in the patent. The size of the crosslinked particles is emphatically restricted to at most 3 $\mu$m and the amount of crosslinked particles to be added is emphatically restricted to at most the concentration associated with a gel point defined in this patent and measured at the processing temperature. This gel point is located at that concentration of crosslinked particles in a solution at which a sharp increase in the viscosity of the solution occurs and the said patent advises against adding higher concentrations of crosslinked particles than those associated with the gel point. The concentration associated with the gel point will depend on the molecular weight of the polymer. Now it has been found that for a solution of crosslinked UHMWPE (HB 312 CM from Himont) with a weight-average molecular weight of $2.6 \times 10^6$ kg/mol in Decalin this gel point lies at a concentration of approximately 5% by weight measured at 140° C. The concentrations of crosslinked polyethylene in the solution according to the present invention range from 3 to 100% and thus in the majority of cases lie far above the gel point. The particle size in which UHMWPE and thus also of crosslinked UHMWPE is commercially available is at least 50 $\mu$m. Since crosslinking normally does not affect the particle size this limitation is also valid for crosslinked UHMWPE. This UHMWPE in crosslinked form can be used in the solution according to the invention without any problems. Thus, in respect of the two points indicated as critical in U.S. Pat. No. 2,908,659, that is to say particle size and concentration of the crosslinked polymer to be used, said patent dissuades those skilled in the art from the solution according to the invention.

Figure 1:
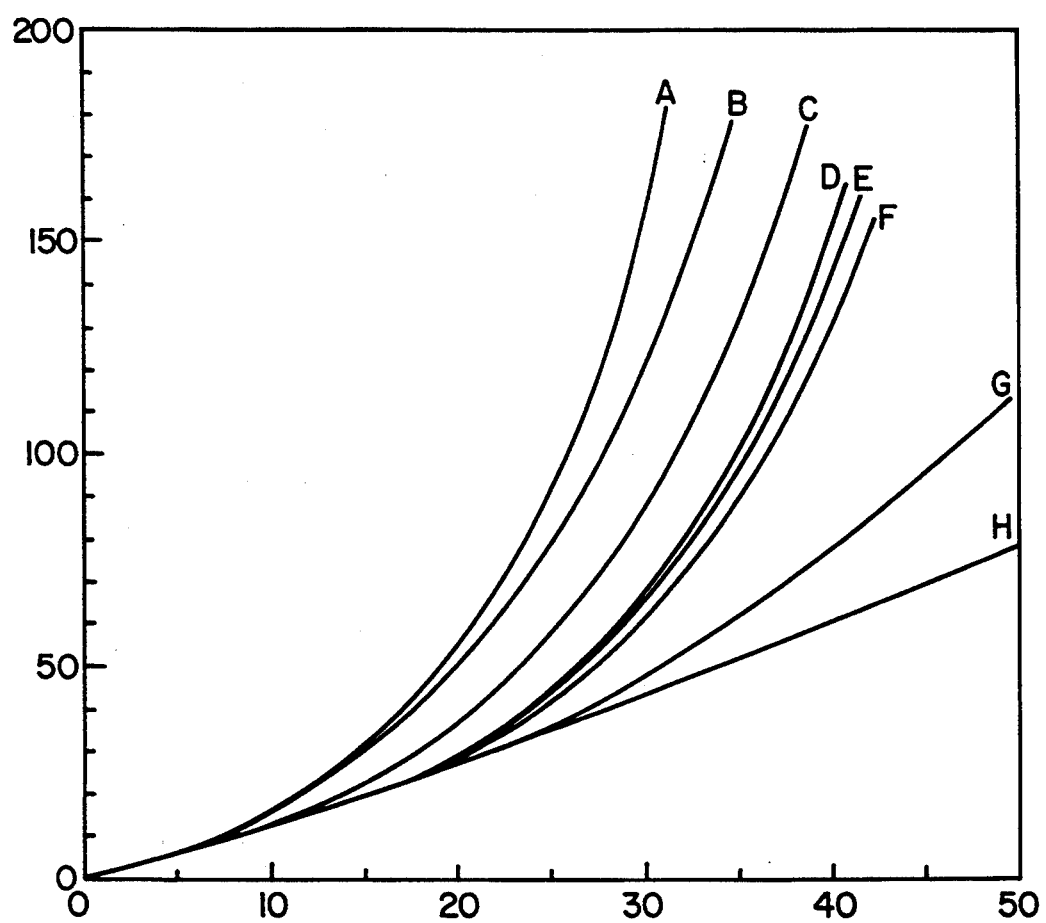
FIG. 1 shows the measured values associated with solutions having the same percentage of added crosslinked UHMWPE for different total concentrations of polyethylene.

The solution according to the invention contains UHMWPE in a concentration of at least 15% by weight. UHMWPE is here understood to be linear polyethylene with less than 1 side chain per 100 carbon atoms and preferably with less than 1 side chain per 300 carbon atoms and a polyethylene of this type which can also contain minor amounts, preferably less than 5 mol-%, of one or more other alkenes copolymerised therewith, such as propylene, butene, pentene, hexene, 4-methyl-pentene, octene, and the like, which polyethylene or copolymer of ethylene has a weight-average molecular weight of at least $0.5 \times 10^6$ kg/kmol. The polyethylene can further contain minor amounts, preferably at most 25% by weight, of one or more other polymers, in particular a 1-alkene polymer, such as polypropylene, polybutene or a copolymer of propylene with a minor amount of ethylene. UHMWPE of this type can be produced, for example, with the aid of a Ziegler process or a Phillips process using suitable catalysts and under known polymerisation conditions.

The weight-average molecular weight of UHMWPE is determined using the methods known for this purpose, such as gel permeation chromatography and light scattering, or is calculated from the intrinsic viscosity (IV) determined in Decalin at 135° C. A weight-average molecular weight of $0.5 \times 10^6$ kg/kmol corresponds to an IV in Decalin at 135° C. of 5.1 dl/g in accordance with the empirical relationship $$M_w = 5.37 \times 10^4 \, [IV]^{1.37}.$$

The organic solvents used are the known solvents for polyolefins, such as aliphatic, cycloaliphatic and aromatic hydrocarbons, such as toluene, xylene, Tetralin, Decalin, $C_6$–$C_{12}$-alkanes or petroleum fractions, but also halogenated hydrocarbons, for example trichlorobenzene and other known solvents, can be applied. In connection with the removal of the solvent, solvents are preferably used for which the boiling point under atmospheric pressure is below 210° C., which is the case for virtually all of the abovementioned solvents.

The way in which the solution is prepared does not constitute part of the invention and this preparation can take place using the techniques known for this purpose, such as, for example, mixing, kneading or stirring, in the known installations suitable for this purpose, or using methods known for the preparation of highly concentrated solutions.

In the case of a total UHMWPE concentration in the solution of below 15% by weight, the fact that some or even all of the UHMWPE is crosslinked is found to have only a slight effect on the processibility of the solution, as reflected in, for example, the pressure generated in the extruder during the extrusion of the solution. In the case of total UHMWPE concentrations in the solution of more than 15% by weight, the advantageous effect of the presence of crosslinked polyethylene (PE) in the solution is found to be clearly expressed in the form of, for example, a lower pressure built up during spinning or extrusion of the solution, and in particular this applies in the case of total UHMWPE concentrations in the solution of more than 20% by weight. Moreover, the effect is found to increase with the percentage of crosslinked UHMWPE relative to the total amount of PE in the solution. A substantial effect is found to occur in the case of percentages of crosslinked polyethylene of from 20%. Preferably, therefore, the amount of crosslinked polyethylene in the solution is 20 to 100% and preferably 30 to 100%, calculated relative to the total amount of polyethylene.

The crosslinking of the UHMWPE can take place using methods known per se, for example, by heating, if desired in the presence of substances which can effect crosslinking, for example, peroxides or silanes in the presence of water, by electron irradiation or by a combination of these measures. Preferably, the crosslinking is effected by electron irradiating of the UHMWPE to be crosslinked in powder form. This method for crosslinking has the advantage that no foreign substances are introduced into the polyethylene during crosslinking, while the powder form of the crosslinked polyethylene obtained is advantageous in bringing the crosslinked polyethylene homogeneously into solution. Preferably, the crosslinking of the UHMWPE takes place at a temperature which is below the melting point of the polyethylene and more preferentially at a temperature below 80° C. Electron irradiation of the polyethylene to be crosslinked at room temperature has been found to be a suitable method for obtaining crosslinked polyethylene suitable for use in the solution according to the invention. If the crosslinking takes place at a temperature above the melting point of the polyethylene, the powder particles melt to form larger conglomerates which are more difficult to bring homogeneously into solution.

Despite the increase in the total polyethylene concentration, the addition of crosslinked polyethylene to the solution of non-crosslinked polyethylene is found to influence the processibility of the solution through a spinning pump or extruder to only a small degree. In particular, this applies in the case of the pressure built up during the spinning or extrusion of the solution from a spinning or extrusion orifice, which pressure as a rule constitutes a limiting factor when processing solutions having these total concentrations using processes known per se. Consequently, a higher total UHMWPE concentration in the solution can be chosen than in the case where only uncrosslinked UHMWPE is present in the solution.

The intrinsic viscosity of the UHMWPE, from which the crosslinked polyethylene has been produced, and of the non-crosslinked UHMWPE can be chosen either identical to one another or different from one another. If the uncrosslinked and the crosslinked UHMWPE differ in this respect, products which possess a combination of the properties of the individual components can be produced by processing the solution according to the invention. If the uncrosslinked polyethylene and the starting material for the crosslinked polyethylene have the same IV, articles produced from the solution according to the invention are found to possess virtually the same advantageous properties as articles produced from a solution of only uncrosslinked polyethylene having the same IV. This applies in particular with regard to the chemical resistance, the stretchability, the creep, the stiffness in flexure, the abrasion resistance and the adhesion properties, in respect of both self-adhesion and adhesion to elastomers. The Vicat softening temperature of these articles is found to be even higher than that of articles produced from a solution in which only the non-crosslinked PE is present.

The solution according to the invention can be used for processing to articles in cases where solutions of uncrosslinked PE can also be used. Examples are the processes known per se for the processing of such solutions to give, for example, filaments, tapes and films, by, for example, extruding and spinning a solution, followed by further processing, for example, removal of the solvent, subjection to a temperature treatment and/or stretching.

The invention is illustrated with the aid of the following examples, without, however, being restricted thereto. The quantities given in the examples are determined as described below.

The Vicat softening temperature is determined in accordance with ASTM standard D1525-76 using a needle pressure of 5 kg.

The stretchability is determined by manual stretching on a hot plate.

The adhesive strength is determined using the 180° peeling test according to DIN 53530.

The tensile strength and the modulus of elasticity are determined from the stress/strain curve measured at room temperature using a Zwick 1435 tensile tester on samples having a clamped length of 50 mm at drawing speed of 50 mm/min.

Example I

Solutions are prepared, in Decalin, of polyethylene (HB 312 CM from Himont) having an IV of 17 dl/g, corresponding to a weight-average molecular weight of $2.6 \times 10^6$ kg/kmol, with different total concentrations of crosslinked and uncrosslinked polyethylene together and for each total concentration with different percentages of uncrosslinked polyethylene relative to the total amount of PE in the solution. The radiation dose during crosslinking is 4–6 MRad. The solutions are prepared with the aid of a twin-screw extruder, to which the polyethylene and the Decalin are fed in the form of a suspension. The pressure which is built up during the extrusion of the solution at 140° C. through a slit having a width of 250 mm and a height of 5 mm is measured. The measured values associated with solutions having the same percentage of added crosslinked UHMWPE for different total concentrations of polyethylene are located on the curves shown in FIG. 1. In FIG. 1 the total UHMWPE concentration in the solution is plotted, in percent by weight relative to the total amount of polyethylene and solvent together, along the horizontal axis and the extruder pressure built up, in bar, is plotted along the vertical axis. The percentage of crosslinked polyethylene relative to the total amount of PE for each curve can be read off from Table 1. It is pointed out that from a total UHMWPE concentration of 15% by weight the influence of the presence of the crosslinked polyethylene with respect to the total amount of PE becomes clearly discernible, in particular in the case of crosslinked polyethylene contents of 20% and above.

TABLE 1

| Curve | Percentage of crosslinked PE |
|---|---|
| A | 0 |
| B | 20 |
| C | 30 |
| D | 50 |
| E | 57 |
| F | 71 |
| G | 86 |
| H | 100 |

Example II

The Vicat softening temperature is determined on a plate-shaped article produced by extrusion in accordance with Example I from a solution of UHMWPE in Decalin followed by cooling of the article and removal of the solvent therefrom by evaporation. The results are given in Table 2.

TABLE 2

| Concentration of UHMWPE in Decalin | Vicat value in °C. |
|---|---|
| 15% uncrosslinked | 80.2 ± 2.8 |
| 20% uncrosslinked | 77.5 ± 1.3 |
| 15% uncrosslinked + 20% crosslinked | 88.4 ± 3.8 |

The Vicat softening temperature is found to be higher when crosslinked UHMWPE is present.

Example III

The stretchability of samples of plate-shaped articles, produced as in Example II, is determined. The results for various concentrations of UHMWPE in the solution used are given in Table 3.

TABLE 3

| Total concentration of uncrosslinked UHMWPE [%] | Total concentration of crosslinked UHMWPE [%] | Stretching temperature [°C.] | Degree of stretching [-] |
|---|---|---|---|
| 20* | 0 | 120 | 15x |
| 20 | 5 | 120 | 15x |
| 20 | 10 | 120 | 16x |
| 20 | 20 | 120 | 15x |

*For comparison

The degree of stretching is found not to decrease when crosslinked UHMWPE is added.

Example V

Using the procedure of Example II, plates are produced from solutions containing various concentrations of crosslinked and non-crosslinked UHMWPE. Each two plates, produced from the same solution, are then pressed against one another under a pressure of 6 bar at a temperature of 140° C. for 6 minutes. The average strength of the mutual adhesion of the plates is given in Table 4.

TABLE 4

| Total concentration of uncrosslinked UHMWPE [%] | Total concentration of crosslinked UHMWPE [%] | Average adhesive power [N/cm] |
|---|---|---|
| 0 | 20 | 202 |
| 0 | 30 | 173 |
| 5 | 30 | 180 |
| 15 | 20 | 162 |
| 20* | 0 | 160 |
| 30* | 0 | 174 |

*For comparison

Example VI

The modulus E and tensile strength σ of plates produced in accordance with Example II is determined before and after pressing at 160° C. and at 200° C. The results are given in Table 5.

TABLE 5

| Total concentration of uncrosslinked UHMWPE [%] | Total concentration of crosslinked UHMWPE [%] | Untreated σ [MPa] | Untreated E [MPa] | Pressed 160° C. σ [MPa] | Pressed 160° C. E [MPa] | Pressed 200° C. σ [MPa] | Pressed 200° C. E [MPa] |
|---|---|---|---|---|---|---|---|
| 15* | 0 | 27 | 1350 | 19 | 300 | 19 | 420 |
| 15 | 20 | 28 | 1160 |  | 550 | 23 | 580 |
| 0 | 20 | 26 | 1290 | 19 | 390 |  |  |

*For comparison

The presence of the crosslinked UHMWPE does not adversely influence the tensile strength and modulus.

We claim:

1. A composition containing ultra-high molecular weight polyethylene and at least one organic solvent wherein the concentration of said ultra-high molecular weight polyethylene is at least 15% by weight, and said ultra-high molecular weight polyethylene comprises crosslinked ultra-high molecular weight polyethylene and non-crosslinked ultra-high molecular weight polyethylene wherein said non-crosslinked ultra-high molecular weight polyethylene is in solution in said organic solvent and said crosslinked ultra-high molecular weight polyethylene is dispersed in said solution, said ultra-high molecular weight polyethylene having a weight-average molecular weight of at least $0.5 \times 10^6$ kg/kmol which corresponds to an intrinsic viscosity (IV) in Decalin at 135° C. of 5.1 dl/g in accordance with the empirical relationship $$M_w = 5.37 \times 10^4 (IV)^{1.37}.$$

2. A composition according to claim 1, wherein said organic solvent is toluene, xylene, Tetralin, Decalin, a $C_6$–$C_{12}$-alkane, a petroleum fraction, or trichlorobenzene.

3. A composition according to claim 1, wherein the concentration of the crosslinked ultra-high molecular polyethylene is at least 20% by weight relative to the total amount of ultra-high molecular weight polyethylene.

4. A composition according to claim 1, wherein said non-crosslinked ultra-high molecular weight polyethylene is present in an amount of at least 15 weight % and said crosslinked ultra-high molecular weight polyethylene is present in an amount of at least 20 wt. % relative to the total amount of ultra-high molecular weight polyethylene.

5. A composition according to claim 1, wherein the intrinsic viscosity of the non-crosslinked ultra-high molecular weight polyethylene is different from the intrinsic viscosity of the crosslinked ultra-high molecular weight polyethylene.

6. A composition according to claim 1, wherein the intrinsic viscosity of the non-crosslinked ultra-high molecular weight polyethylene is the same as the intrinsic viscosity of the crosslinked ultra-high molecular weight polyethylene.

7. A composition according to claim 1, wherein said crosslinked ultra-high molecular weight polyethylene was crosslinked at a temperature below 80° C.

8. A composition according to claim 1, wherein said crosslinked ultra-high molecular weight polyethylene was obtained by irradiating a non-crosslinked ultra-high molecular weight polyethylene at room temperature.

9. A composition according to claim 8, wherein said crosslinked ultra-high molecular weight polyethylene was obtained by subjecting a powder consisting of non-crosslinked ultra-high molecular weight polyethylene to electron irradiation.

10. A composition according to claim 1, wherein the ultra-high molecular weight polyethylene has a weight-average molecular weight of $2.6 \times 10^6$ kg/kmol.

11. A process for preparing an article from a composition according to claim 1, which process comprises extruding or spinning said composition to obtain an article, and removing the organic solvents from the article.

12. A process according to claim 11, wherein a composition according to claim 9 is extruded to obtain an extruded article and the solvent is removed therefrom.

13. A process according to claim 11, further comprising stretching the extruded article before or after removing the solvent.

14. A process according to claim 11, wherein a composition according to claim 9 is spun to obtain a spun article and the solvent is removed therefrom.

15. A process according to claim 14, further comprising stretching the spun article before or after removing the solvent.

16. A composition containing an ultra-high molecular weight ethylene (co)polymer and at least one organic solvent, wherein said ultra-high molecular weight ethylene (co)polymer contains less than 5 mole percent of at least one alkene selected from the group consisting of propylene, butene, pentene, hexene, 4-methyl-petene and octene, said ultra-high molecular weight ethylene (co)polymer having a weight-average molecular weight of at least $0.5 \times 10^6$ kg/kmol which corresponds to an intrinsic viscosity (IV) in Decalin at 135° C. of 5.1 dl/g in accordance with the empirical relationship $$M_w = 5.37 \times 10^4 [IV]^{1.37},$$

wherein the concentration of the ultra-high molecular weight ethylene (co)polymer is at least 15% by weight, and said ultra-high molecular weight ethylene (co)polymer consists of crosslinked ultra-high molecular weight ethylene (co)polymer and non-crosslinked ultra-high molecular weight ethylene (co)polymer wherein said non-crosslinked ultra-high molecular weight ethylene (co)polymer is in solution in said organic solvent and said crosslinked ultra-high molecular weight ethylene (co)polymer is dispersed in said solution.

17. A composition containing an ultra-high molecular weight ethylene (co)polymer and at least one organic solvent, wherein said ultra-high molecular weight ethylene (co)polymer contains less than 5 mole percent of at least one alkene selected from the group consisting of propylene, butene, pentene, hexene, 4-methyl-petene and octene, said ultra-high molecular weight ethylene (co)polymer having a weight-average molecular weight of at least $0.5 \times 10^6$ kg/kmol which corresponds to an intrinsic viscosity (IV) in Decalin at 135° C. of 5.1 dl/g in accordance with the empirical relationship $$M_w = 5.37 \times 10^4 [IV]^{1.37},$$

wherein the concentration of the ultra-high molecular weight ethylene (co)polymer is at least 15% by weight, and said ultra-high molecular weight ethylene (co)polymer consists of crosslinked ultra-high molecular weight polyethylene in an amount of 20%–100% by weight and 80% to 0% by weight non-crosslinked ultra-high molecular weight polyethylene, wherein said non-crosslinked ultra-high molecular weight ethylene (co)polymer is in solution in said organic solvent and said crosslinked ultra-high molecular weight ethylene (co)polymer is dispersed in said solution, and wherein said % by weight being relative to the total amount of ultra-high molecular weight ethylene (co)polymer in solution.

18. An ultra-high molecular weight polyolefin composition comprising at least one organic solvent and an ultra high molecular weight polyolefin selected from the group consisting of ultra-high molecular weight ethylene homopolymer, ultra-high molecular weight ethylene copolymer, and mixtures thereof, said ultra-high molecular weight ethylene copolymer and said ethylene homopolymer each have a weight-average molecular weight of at least $0.5 \times 10^6$ kg/kmol which corresponds to an intrinsic viscosity (IV) in Decalin at 135° C. of 5.1 dl/g in accordance with the empirical relationship $$M_w = 5.37 \times 10^4 [IV]^{1.37},$$

the concentration of said polyolefin is at least 15% by weight, said ethylene copolymer is selected from the group consisting of crosslinked ultra-high molecular weight ethylene copolymer and non-crosslinked ultra-high molecular weight ethylene copolymer, said ultra-high molecular weight ethylene homopolymer is selected from the group consisting of crosslinked ultra-high molecular weight ethylene homopolymer and non-crosslinked ultra-high molecular weight ethylene homopolymer, said composition contains at least one crosslinked member selected from the group consisting of crosslinked ultra-high molecular weight ethylene copolymer and crosslinked ultra-high molecular weight ethylene homopolymer, said composition contains at least one non-crosslinked member selected from the group consisting of non-crosslinked ultra-high molecular weight ethylene copolymer and non-crosslinked ultra-high molecular weight ethylene homopolymer, and said non-crosslinked member is in solution in said organic solvent and said crosslinked member is dispersed in said solution.

19. A composition according to claim 18, wherein said ultra-high molecular weight ethylene (co)polymer contains less than 5 mole percent of at least one alkene selected from the group consisting of propylene, butene, pentene, hexene, 4-methyl-pentene and octene.

* * * * *